United States Patent
Daniel et al.

(10) Patent No.: US 12,178,481 B2
(45) Date of Patent: Dec. 31, 2024

(54) BONE PLATES HAVING MULTI-USE COMBINATION HOLES FOR LOCKING AND DYNAMIC COMPRESSION, AND RELATED SYSTEMS AND METHODS

(71) Applicant: DePuy Synthes Products, Inc., Raynham, MA (US)

(72) Inventors: Steffan Daniel, Solothurn (CH); This Aebi, Grenchen (CH); Andreas Baeriswyl, Büren an der Aare (CH); Joel Oberli, Niederdorf (CH); Mirko Rocci, Bettlach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/155,218

(22) Filed: Jan. 22, 2021

(65) Prior Publication Data
US 2022/0233220 A1    Jul. 28, 2022

(51) Int. Cl.
*A61B 17/80*    (2006.01)

(52) U.S. Cl.
CPC ...... *A61B 17/8014* (2013.01); *A61B 17/8057* (2013.01)

(58) Field of Classification Search
CPC .................................................. A61B 17/8014
See application file for complete search history.

(56) References Cited

U.S. PATENT DOCUMENTS

| | | | |
|---|---|---|---|
| 6,669,701 B2 | 12/2003 | Steiner et al. | |
| 6,719,759 B2 | 4/2004 | Wagner et al. | |
| 6,730,091 B1 | 5/2004 | Pfefferle et al. | |
| (Continued) | | | |

FOREIGN PATENT DOCUMENTS

| | | |
|---|---|---|
| AU | 2011200981 A1 | 9/2011 |
| CN | 101703420 A | 5/2010 |
| (Continued) | | |

OTHER PUBLICATIONS

Entitled Threaded Locking Structures for Affixing Bone Anchors to a Bone Plate, and Related Systems and Methods, filed Apr. 30, 2018, U.S. Appl. No. 15/966,047.

(Continued)

*Primary Examiner* — Olivia C Chang
(74) *Attorney, Agent, or Firm* — BakerHostetler

(57) ABSTRACT

A bone plate includes a plate body defining an interior surface that defines a combination hole that includes intersecting locking and compression holes that each extend between outer and bone-facing surfaces of the plate body. A central axis of the compression hole is spaced from a central axis of the locking hole in an offset direction. A locking surface of the plate body defines the locking hole and at least one locking structure therein. A compression surface of the plate body defines the compression hole. An intersection boundary between the locking and compression surfaces is configured to translate the bone plate in the offset direction during contact between the intersection boundary and a head of a compression screw as it advances within the combination hole along an insertion axis offset from the central axis of the locking hole at an offset distance in a direction having a directional component in the offset direction.

16 Claims, 6 Drawing Sheets

(56) References Cited

U.S. PATENT DOCUMENTS

| | | |
|---|---|---|
| 7,354,441 B2 | 4/2008 | Frigg |
| 7,695,502 B2 | 4/2010 | Orbay et al. |
| 7,776,076 B2 | 8/2010 | Grady et al. |
| 7,951,176 B2 | 5/2011 | Grady et al. |
| 7,976,570 B2 | 7/2011 | Wagner et al. |
| 8,343,196 B2 | 1/2013 | Schneider |
| 8,758,346 B2 | 6/2014 | Koay et al. |
| 8,845,698 B2 | 9/2014 | Schneider |
| 8,852,245 B2 | 10/2014 | Schneider |
| 8,876,873 B2 | 11/2014 | Schneider |
| 8,940,029 B2 | 1/2015 | Leung et al. |
| 9,107,711 B2 | 8/2015 | Hainard |
| 9,161,791 B2 | 10/2015 | Frigg |
| 9,295,505 B2 | 3/2016 | Schneider |
| 9,308,034 B2 | 4/2016 | Grady et al. |
| 9,314,284 B2 | 4/2016 | Chan et al. |
| 9,931,148 B2 | 4/2018 | Grady et al. |
| 10,231,768 B2 | 3/2019 | Grady et al. |
| 10,342,586 B2 | 7/2019 | Schneider |
| 10,653,466 B2 | 5/2020 | Grady et al. |
| 10,772,665 B2 | 9/2020 | Bosshard et al. |
| 2002/0183752 A1 | 12/2002 | Steiner et al. |
| 2004/0049196 A1 | 3/2004 | Jackson |
| 2008/0161860 A1* | 7/2008 | Ahrens .............. A61B 17/8014 606/280 |
| 2009/0312803 A1 | 12/2009 | Austin et al. |
| 2012/0264528 A1 | 10/2012 | Isobe et al. |
| 2012/0265255 A1 | 10/2012 | Hilse et al. |
| 2014/0018862 A1 | 1/2014 | Koay et al. |
| 2014/0207194 A1 | 7/2014 | Wolter |
| 2014/0316473 A1 | 10/2014 | Pfeiffer et al. |
| 2016/0367299 A1 | 12/2016 | Paolino et al. |
| 2018/0003212 A1 | 1/2018 | Seo et al. |
| 2018/0064477 A1 | 3/2018 | Lopez et al. |
| 2018/0132913 A1 | 5/2018 | Davison et al. |
| 2018/0161081 A1 | 6/2018 | Anding et al. |
| 2018/0250043 A1 | 9/2018 | Rapalo et al. |
| 2018/0310972 A1* | 11/2018 | Anding .............. A61B 17/8605 |
| 2019/0269444 A1 | 9/2019 | Schneider |
| 2019/0328430 A1 | 10/2019 | Bosshard et al. |
| 2020/0237420 A1 | 7/2020 | Grady et al. |
| 2020/0390483 A1 | 12/2020 | Oberli et al. |
| 2021/0015526 A1 | 1/2021 | Oberli et al. |

FOREIGN PATENT DOCUMENTS

| | | |
|---|---|---|
| CN | 201861741 U | 6/2011 |
| CN | 102188282 A | 9/2011 |
| CN | 103961173 A | 8/2014 |
| CN | 105232131 A | 1/2016 |
| DE | 102015102629 B4 | 10/2022 |
| EP | 2919688 A1 | 9/2015 |
| JP | 2006-511252 A | 4/2006 |
| JP | 2010-536427 A | 12/2010 |
| WO | 2006/014436 A1 | 2/2006 |
| WO | 2011/078365 A1 | 6/2011 |
| WO | 2013/036362 A1 | 3/2013 |
| WO | 2014/078289 A1 | 5/2014 |
| WO | 2019/211681 A1 | 11/2019 |
| WO | 2020/234669 A1 | 11/2020 |
| WO | 2020/250052 A1 | 12/2020 |

OTHER PUBLICATIONS

Entitled, Locking Structures for Affixing Bone Anchors to a Bone Plate, and Related Systems and Methods, filed Mar. 29, 2018, U.S. Appl. No. 15/940,761.

U.S. Appl. No. 63/107,699, filed Oct. 30, 2020 entitled Bone Plates Having Multi-Use Screw Holes for Locking and Compression Screws, and Related Systems and Methods.

"General Administration of Quality Supervision, Inspection and Quarantine of the People's Republic of China", National Standard of the People's Republic of China GB/T 192-2003, No. 192-2003 Edition, May 22, 2023, pp. 423-424.

* cited by examiner

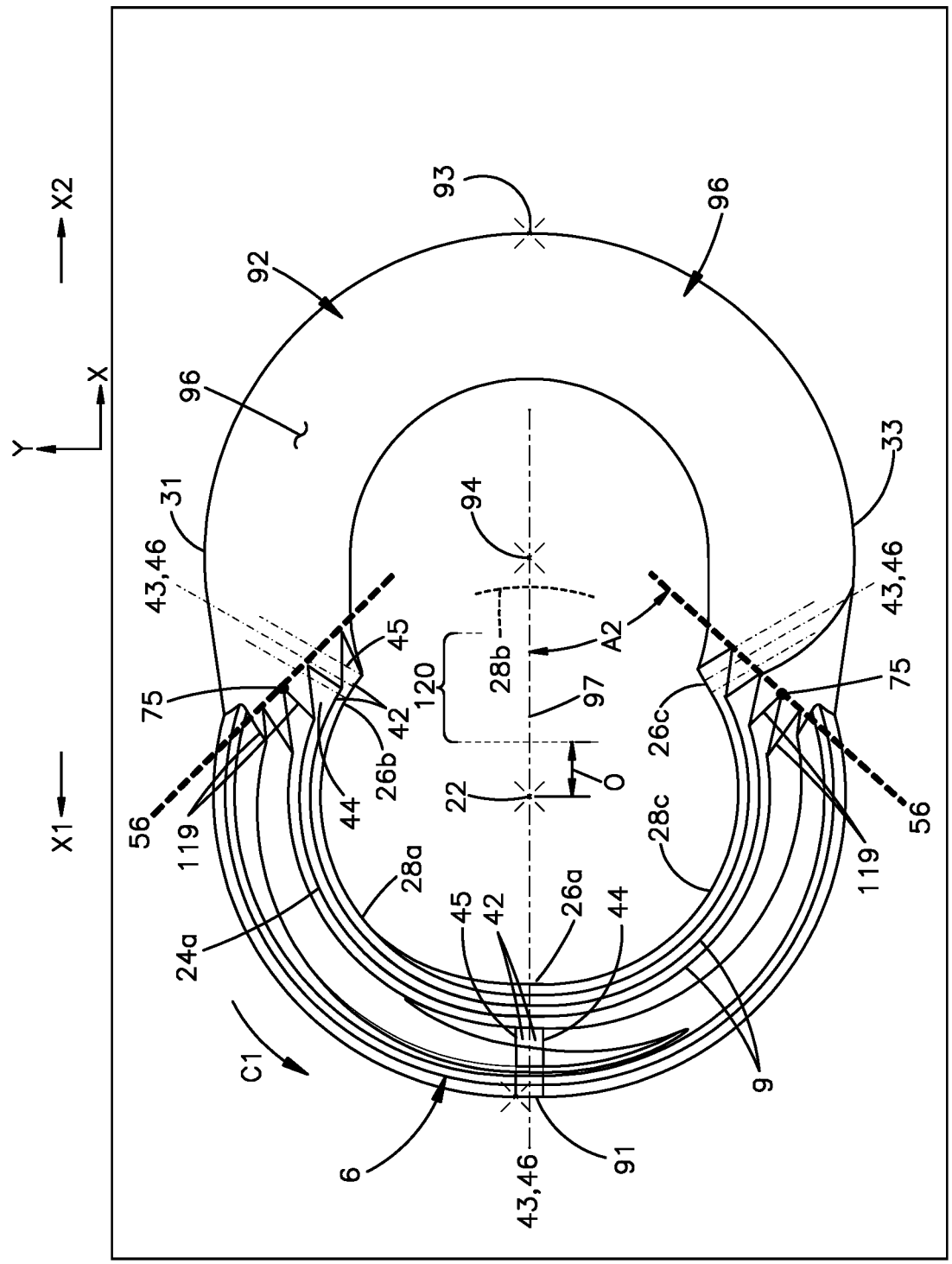

BONE PLATES HAVING MULTI-USE COMBINATION HOLES FOR LOCKING AND DYNAMIC COMPRESSION, AND RELATED SYSTEMS AND METHODS

TECHNICAL FIELD

The present invention relates to bone plates for receiving bone anchors to affix the bone plates to bone, and particularly relates to bone plates having combination holes defined by a locking hole intersected by a compression hole, more particularly such that the intersecting geometries thereof are configured to translate the bone plate in a direction from the compression hole toward the locking hole when a head of a compression bone anchor is driven eccentrically within the locking hole.

BACKGROUND

Bone plate systems for the internal fixation of bone fractures are well known. Conventional bone plate systems are particularly well-suited to promote the healing of a fracture. A bone anchor, such as a bone screw, is inserted through a fixation aperture or hole in a bone plate and is threaded into bone to compress, neutralize, buttress, tension, band, and/or bridge the fracture ends together. Bone screws that are capable of locking with the bone plate can be employed to transfer loads from one fractured bone part, over a plate, and onto another fractured bone part without drawing the bone against the plate, and to avoid loosening or backing out the bone screws with respect to the plate (which can lead to poor alignment and poor clinical results). One known embodiment of such a screw employs a screw head with external threads for engaging with a corresponding thread on the inner surface of a fixation hole, which are hereinafter referred to as "locking holes", to lock the screw to the plate. These screws, which are hereinafter referred to as "locking screws", can include standard-type locking screws that are configured to lock within a fixation hole substantially only at a "nominal" orientation whereby the central screw axis is substantially aligned with the central hole axis, as well as "variable-angle" (VA) locking screws that are configured to lock within a fixation hole at either a nominal orientation or an "angulated" orientation whereby the central screw axis is oriented at an acute angle with respect to the respective central hole axis.

Bone plate systems can also be adapted to provide anatomical reduction between fractured bone parts. The bone plates of such systems include one or more holes having ramp geometries that engage a smooth exterior surface of a screw head of a "compression screw" in a manner causing dynamic compression, meaning that the bone plate translates with respect to the compression screw and underlying bone along a direction generally perpendicular to the screw axis of the compression screw. Such holes are hereinafter referred to as "compression holes". Bone plates can include both locking holes and compression holes. Additionally or alternatively, bone plates can include combination holes or "combi-holes" that include a locking hole and a compression hole that intersect one another, such that the locking hole and the compression hole overlap one another and are open to each other. Combi-holes are commonly used selectively for either locking the plate to underlying bone (by inserting a locking screw within the locking hole of the combi-hole) or translating the plate relative to the underlying bone (by inserting a compression screw within the compression hole of the combi-hole).

SUMMARY

According to an embodiment of the present disclosure, a bone plate includes a plate body that defines an interior surface that defines a combination hole that includes a locking hole and a compression hole that intersect one another. The locking hole and the combination hole each extends from an outer surface of the plate body to a bone-facing surface of the plate body. The locking hole defines a central locking hole axis and the compression hole defines a central compression hole axis that is spaced from the central locking hole axis in an offset direction. The plate body further defines a locking surface that defines the locking hole and at least one locking structure therein. The plate further defines a compression surface that defines the compression hole. An intersection boundary between the locking surface and the compression surface is configured to cause translation of the bone plate in the offset direction responsive to contact between the intersection boundary and an exterior surface of a head of a compression screw as the head advances within the combination hole along an insertion axis that is offset from the central locking hole axis at an offset distance measured in a direction having a directional component in the offset direction.

According to another embodiment of the present disclosure, a method of seating a bone screw in a combination hole defined by an interior surface of a bone plate includes inserting a shaft of the compression screw through a locking hole of the combination hole and into underlying bone. The locking hole is intersected by a compression hole. The shaft is inserted through the locking hole at an offset distance measured from a central locking hole axis of the locking hole toward a central screw axis of the compression screw in an offset direction. The offset direction extends from the central locking hole axis toward a central compression hole axis of the compression hole. The method includes contacting an outer surface of the head of the compression screw against opposite sides of the combination hole spaced from each other along a lateral direction that is substantially perpendicular to the offset direction. The method includes driving the bone screw, during the contacting step, toward the underlying bone along the central screw axis, responsively sliding the head along respective contact paths along the opposite sides, wherein the respective contact paths each have a directional component in the offset direction, thereby translating the bone plate in the offset direction relative to the bone screw.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings:

FIG. 1C is another top plan view of the bone plate illustrated in FIG. 1A;

DETAILED DESCRIPTION OF ILLUSTRATIVE EMBODIMENTS

Figure 1A:
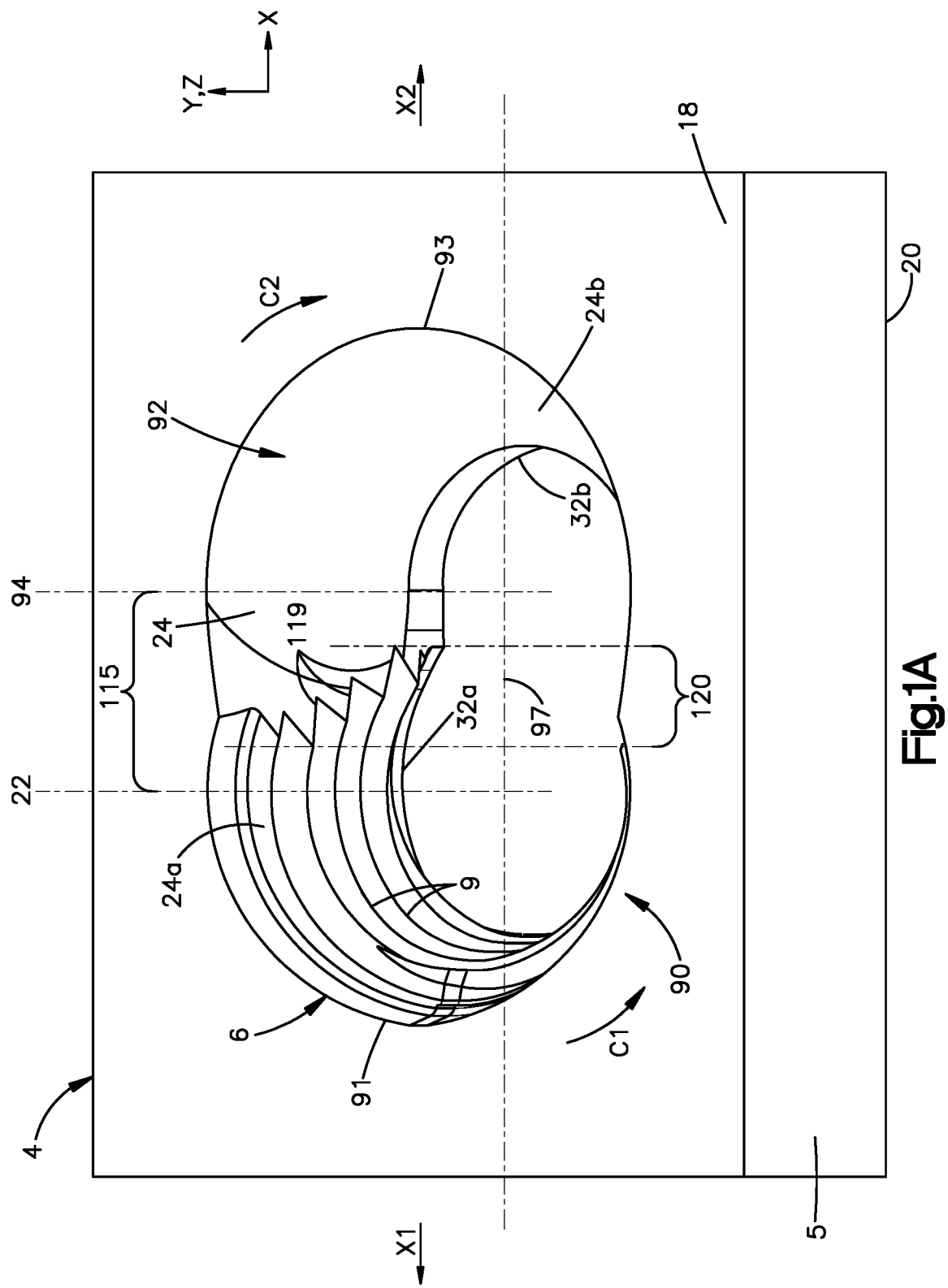
FIG. 1A is a perspective view of a bone plate that defines a combi-hole, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately", "about", and "substantially", as used herein with respect to dimensions, angles, ratios, and other geometries, takes into account manufacturing tolerances. Further, the terms "approximately", "about", and "substantially" can include 10% greater than or less than the stated dimension, ratio, or angle. Further, the terms "approximately", "about", and "substantially" can equally apply to the specific value stated.

As used herein, the term "dynamic compression" refers to an act of engaging a bone anchor against a bone plate in a manner causing the bone plate to translate relative to the bone anchor and underlying patient anatomy (e.g., underlying bone) along a direction that is generally perpendicular to an axis along which the bone anchor is inserted into underlying bone.

The embodiments disclosed herein pertain to combi-holes in a bone plate. The combi-holes include a locking hole intersected by a compression hole. The locking hole and compression hole have respective geometries such that a non-locking bone anchor (e.g., a "cortex screw" or "compression screw") inserted along an "eccentric" insertion axis (i.e., an insertion axis offset from a central axis of the locking hole) that is offset in an offset direction toward a central axis of the compression hole will cause the head of the compression screw to engage an intersection boundary between the locking and compression holes. Such contact between the head and the intersection boundary, as the head is driven toward the underlying bone, causes dynamic compression (i.e., translates the bone plate relative to the underlying bone) in a direction having a directional component in the offset direction. Dynamic compression is particularly useful for moving fractured portions of bone relative to one another, such as for anatomical reduction to treat bone fractures. The combi-holes of the present disclosure provide a physician with additional options for achieving dynamic compression, particularly by inserting the compression screw within the compression hole to translate the plate in a first direction and inserting the compression screw within the locking hole to translate the plate in a second direction, such as opposite the first direction.

The inventors have discovered, surprisingly and unexpectedly, that the threaded locking holes of combi-holes having certain geometries can be alternatively used with compression bone anchors to achieve dynamic compression, even when the head of the compression bone anchor contacts the interior plate surface within the locking hole, even when the contact occurs over and/or along the internal threads in the locking hole. Thus, the combi-holes of the present disclosure include intersecting locking holes and compression holes having respective geometries such that an intersection boundary therebetween can provide dynamic compression when a compression bone anchor, such as a compression screw, is inserted within the locking hole eccentrically toward the compression hole. In these combi-holes, the primary direction of dynamic compression (i.e., plate translation) is generally from the compression hole toward the locking hole, which is the opposite of most prior art combi-holes. For this reason, the combi-holes of the present disclosure can be characterized as "reverse combi-holes." Furthermore, the combi-holes of the present disclosure can increase the overlap between the locking and compression holes thereof, thereby reducing a longitudinal length of the combi-hole, which can allow a higher combi-hole density within a bone plate (i.e., more combi-holes to be employed within the same plate area relative to prior art combi-holes). Additionally, such higher hole density, in combination with the enhanced dynamic compression options for each combi-hole, provides enhanced options for patient-specific fracture fixation treatment, which provides further advantages in that such treatments can be less invasive and require a shorter healing and recovery period.

Figure 1B:
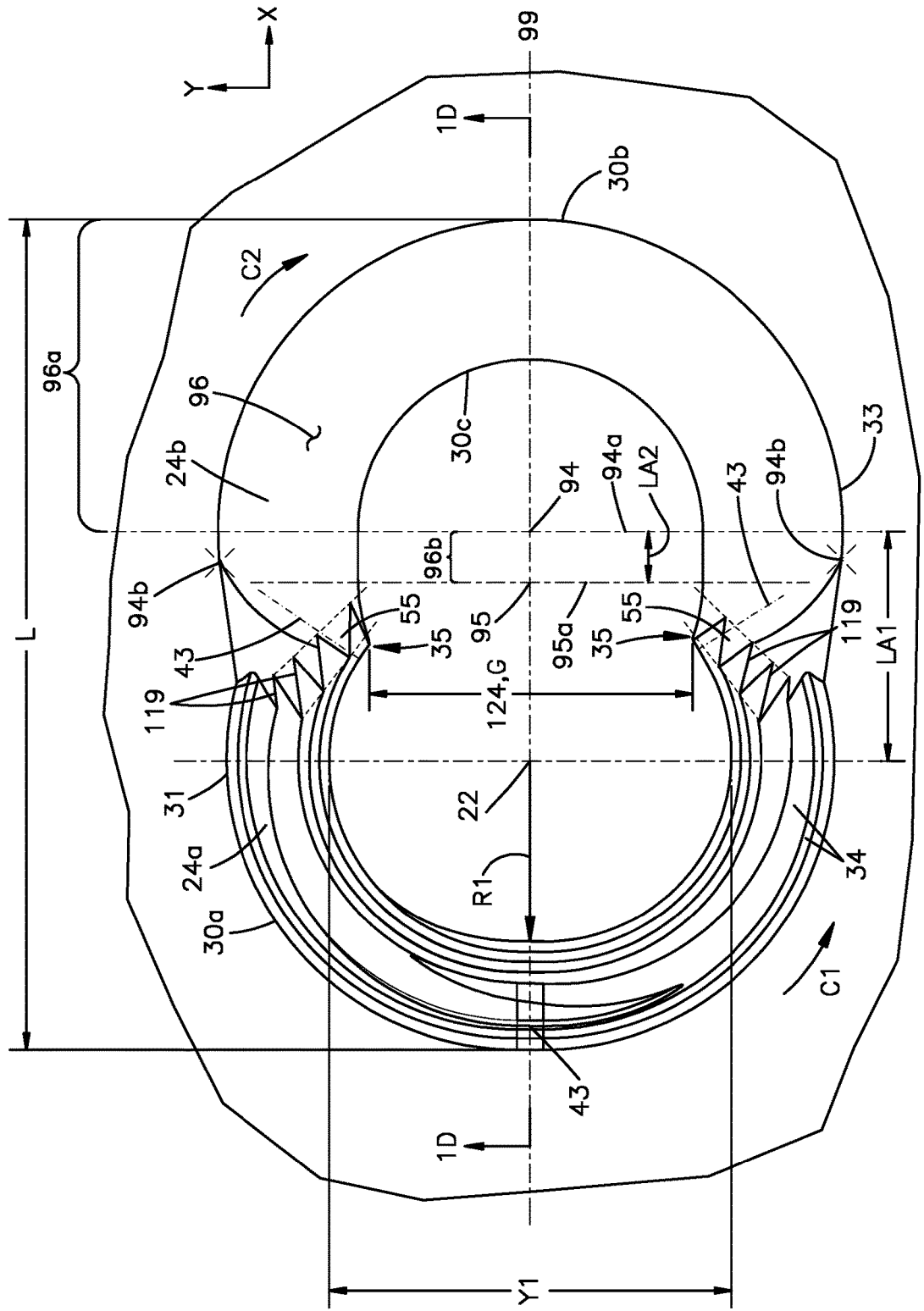
FIG. 1B is a top plan view of the bone plate illustrated in FIG. 1A.

Referring to FIGS. 1A and 1B, a bone plate 4 has a plate body 5 that defines therein at least one combination hole or "combi-hole" 90 that extends from an upper surface 18 of the plate body 5 to a bone-facing surface 20 of the plate body 5. The plate body 5 defines an interior surfaces 24 that defines the combi-hole 90. In particular, the interior surface 24 defines a locking hole 6 and a compression hole 92 that intersect and overlap one another so as to provide the combi-hole 90. The locking hole 6 extends from the upper surface 18 to the bone facing surface 20 of the plate body 5 along a central locking hole axis 22. The compression hole 92 extends from the upper surface 18 to the bone facing surface 20 along a central compression hole axis 94. The central locking hole axis 22 and the central compression hole axis 94 axis are preferably parallel, although in other embodiments these axes 22, 94 can be angularly offset from each other at an acute angle.

The combi-hole 90 defines a first end 91 and a second end 93 spaced from each other at a hole length L along a first direction, which is also referred to herein as a longitudinal direction X. In particular, the first end 91 is spaced from the second end 93 in a first longitudinal direction X1, while the second end 93 is spaced from the first end 91 in a second longitudinal direction X2 opposite the first longitudinal direction X2. It should be appreciated that the first and second longitudinal directions X1, X2 each refer to mono-directional components of the longitudinal direction X, which is bi-directional. The locking hole 6 and the compression hole 92 can be characterized as extending toward and away from each other along the longitudinal direction X. The combi-hole 90 defines an intersection axis 97 that intersects both axis 22 and axis 94. Axis 22 and axis 94 are spaced from each other at an axis separation distance LA1, preferably measured along the longitudinal direction X. In such embodiments, the intersection axis 97 is oriented along the longitudinal direction X and can thus also define a longitudinal axis of the combi-hole 90. The combi-hole 90 also defines a first side 31 and a second side 33 spaced from each other along a second direction, also referred to herein as a lateral direction Y, which is substantially perpendicular to the longitudinal direction X. The combi-hole 90 defines a total depth D1 (FIG. 1C) measured from the upper surface 18 to the bone-facing surface 20 along a third direction, also referred to herein as a transverse direction Z, which is substantially perpendicular to the longitudinal and lateral, directions X, Y. As used herein, the term "depth" refers to a distance within the combi-hole 90 as measured from the upper surface 18 of the plate 4 toward the lower surface 20 thereof along the transverse direction Z.

It should be appreciated that the longitudinal, lateral, and transverse directions X, Y, Z used herein refer to spatial aspects of the structure(s) in three-dimensional space, and are not affected by the orientation of the bone plate 4 relative to other physical structure. For example, the upper and bone-facing surfaces 18, 20 of the plate body 5 remain spaced from each other along the transverse direction Z regardless of the orientation of the plate body 4 relative to a patient. It should also be appreciated that, as used herein, the terms "longitudinal", "longitudinally", and derivatives thereof refer to the longitudinal direction X; the terms "lateral", "laterally", and derivatives thereof refer to the lateral direction Y; and the terms "transverse", "transversely", and derivatives thereof refer to the transverse direction Z. Moreover, a plane extending along the longitudinal and laterals directions X, Y can be referred to herein as a longitudinal-lateral plane X-Y or "horizontal" plane X-Y. Similarly, a plane extending along the longitudinal and transverse directions X, Z can be referred to herein as a longitudinal-transverse plane X-Z; and a plane extending along the lateral and transverse directions Y, Z can be referred to herein as a lateral-transverse plane Y-Z.

The central locking hole axis 22 is oriented along an axial locking hole direction. The central compression hole axis 94 is oriented along an axial compression hole direction. As used herein, the terms "axial" in conjunction with "direction" (e.g., "axial hole direction", "axial locking hole direction", "axial compression hole direction", and "axial screw direction") refers to the direction along which the respective axis extends. Furthermore, the directional terms "axial", "axially", and derivatives thereof refer to the respective axial direction. Thus, as used herein, the directional terms "axially upward", "upward", and derivatives thereof refer to the respective axial hole direction from the lower plate surface 20 toward the upper plate surface 18. Conversely, the terms "axially downward", "downward", and derivatives thereof refer to the respective axial hole direction from the upper plate surface 18 toward the lower plate surface 20. Thus, "axially upward" and "axially downward" (and their respective derivatives) each refer to mono-directional components of the respective "axial hole direction" or "axial screw direction", which are bi-directional. In the embodiments depicted in the Figures, the axial hole directions are oriented along the transverse direction Z. Accordingly, the axial hole directions can be denoted by "Z" throughout this disclosure. It should be appreciated, however, that the scope of the present disclosure covers embodiments in which one or more of the axial hole directions (and thus also the respective hole axis 22, 94) is offset from the transverse direction Z at an acute angle. It should also be appreciated that when the terms "axially upper", "axially lower," and the like are used with reference to a bone anchor, such as a compression screw 7, such terms refer to a central axis 52 of the screw, particularly as the screw would be oriented within the combi-hole 90.

A portion of the interior surface 24 that defines the locking hole 6 is referred to herein as a "locking surface" 24a, while a portion of the interior surface 24 that defines the compression hole 92 is referred to herein as a "compression surface" 24b. The locking surface 24a and the compression surface 24b each extend from the upper surface 28 to the bone-facing surface 20 of the plate body 5. The locking and compression surfaces 24a, 24b can define respective upper perimeters 30a, 30b at an interface with the upper plate surface 18 and can further define respective lower perimeters 32a, 32b at an interface with the lower plate surface 20. The locking and compression surfaces 24a, 24b intersect each other along an intersection boundary 119 along the first and second sides 31, 33 of the combi-hole 90. The interior surface 24 also defines a hole intersection zone 120 in which the intersection boundary 119 is located.

The locking and compression surfaces 24a, 24b each revolve about their respective axis 22, 94 along respective circumferential directions C1, C2 from the intersection boundary 119 on the first side 31 to the intersection boundary 119 on the second side 33. As used herein with reference to the locking surface 24a and the compression surface 24b, the term "circumference" refers to a path that extends along the respective surface 24a, 24b in revolving fashion between the intersection boundary 119 on the first side 31 and the intersection boundary 119 on the second side 33 (irrespective of the fact that the locking and compression surfaces 24a, 24b do not complete a full revolution about their respective axis 22, 94). It should be appreciated that, as used herein, the terms "circumferential", "circumferentially", and derivatives thereof refer to the respective circumferential direction C1, C2.

The first and second sides 31, 33 extend laterally toward each other along the intersection boundary 119, such that the interior surface 24 defines a neck 35 at the intersection boundary 119. A gap 124 extends laterally between the first and second sides 31, 33 at the neck 35. The locking hole 6 and the compression hole 92 are open to each other through the gap 124. The combi-hole 90 further defines an intermediate zone 115 between the central locking hole axis 22 and the central compression hole axis 94. In particular, the intermediate zone 115 extends longitudinally from axis 22 to axis 94. In three-dimensional space, the intermediate zone 115 also extends laterally from the first side 31 to the second side 33 of the combi-hole 90 and transversely from the upper surface 18 to the bone-facing surface 20. The intermediate zone 115 thus defines the space between axes 22 and 94 with respect to the longitudinal direction X. The combi-hole 90 of the present embodiment is configured such that, within the intermediate zone 115, a minimum lateral dimension G between the first and second sides 31, 33 occurs at the gap 124 of the neck 35. In such embodiments, the minimum lateral dimension can be referred to as the "gap width" G.

The locking surface 24a defines at least one locking structure within the locking hole 6. The at least one locking structure can include internal threads 9 that are configured to threadedly engage (i.e., intermesh with) external threads on a head of a locking bone screw in a manner allowing the intermeshed threads to lock to each other, thus locking the locking bone screw at a specific orientation relative to the bone plate 4. The at least one locking structure (e.g, internal threads 9) can be configured to lock with the external threads of standard-type locking screws and/or variable-angle" (VA) locking screws. Standard-type locking screws are configured to lock within the locking hole 6 substantially only at a "nominal" orientation whereby the central axis of the locking screw (also referred to herein as the "central screw axis") is substantially aligned with the central locking hole axis 22. VA locking screws are configured to lock within the locking hole 6 selectively at either a nominal orientation or an "angulated" orientation, whereby the central screw axis is oriented at an acute angle with respect to the central locking hole axis 22. Such angulated orientations are also referred to herein as "angulation." Although the at least one locking structure of the illustrated embodiments are threads 9, it should be appreciated that the locking surface 24a can employ other locking structure types can be employed, such as ribs, projections, recesses, and the like, which can optionally be configured to deform responsive to engagement with the head of a locking screw in a manner locking the head to the plate body 5 within the locking hole 6.

The internal threads 9 can be located at a transversely intermediate region of the locking hole 6 (i.e., a region spaced from both the upper surface 18 and the bone-facing surface 20 of the locking hole 6). The locking surface 24a can define one or more lead-in surfaces 34 that extend from the upper perimeter 30a and downward to the threads 9. The locking surface 24 can also define at least one undercut surfaces 36a (also referred to herein as a "relief surface") that extends axially upward from the lower perimeter 32a toward the threads 9. The threads 9 can extend axially between the lead-in surface(s) 34 and the undercut surface(s) 36. As shown, the threads 9 can traverse at least portions of the lead-in surface(s) 34 and/or undercut surface(s) 36.

The internal threads 9 revolve around the central locking hole axis 22 along one or more thread paths between the upper and bone-facing surfaces 18, 20 of the plate 4. The threads 9 preferably extend continuously along the circumference of the locking surface 24a, interrupted substantially only by the gap 124. In other embodiments, the threads 9 can extend non-continuously along the circumference of the locking surface 24a. It should be appreciated that the threads 9 can be configured similar to those disclosed in U.S. patent application Ser. No. 16/437,105, filed Jun. 11, 2019, in the name of Oberli et al. ("the '105 Reference" [7683]), and U.S. patent application Ser. No. 17/062,708, filed Oct. 5, 2020, in the name of Oberli et al. ("the '708 Reference"), the entire disclosures of each of which are hereby incorporated by reference herein.

The locking surface 24a is preferably configured for locking with both standard-type and VA locking screws. For example, the locking surface 24a can define at least one column 26, and preferably also defines at least portions of additional columns 26 sequentially located about a circumference of the locking surface 24a. The locking surface 24a can also define a plurality of recesses 28 sequentially located circumferentially between the column 26 and the at least the portions of the additional columns 26. As shown in FIG. 1C, the locking surface 24a can define a first column 26a, at least a portion of second column 26b, and at least a portion of a third column 26c. In the present embodiment, the remainder of the second and third columns 26b, 26c have effectively been removed by the intersection of the locking and compression holes 6, 92. Thus, the intersection boundary 119 traverses portions of the second and third columns 26b, 26c. For example, the intersection boundary 119 can traverse entireties of the second and third columns 26b, 26c with respect to the circumferential direction C1. Moreover, at least some of the threads 9 along each of the first and second sides 31, 33, such as threads 9 that traverse the second and third columns 26b, 26c, preferably extend to the intersection boundary 119 such that interface edges between the locking surface 24a and the compression surface 24b include edges of fully formed thread profiles (i.e., from root to crest) of the threads 9.

The first, second, and third columns 26a-c can each be centered along a respective column centerline 43 as viewed in a horizontal plane X-Y. The columns centerlines 43 are preferably oriented to intersect the central locking hole axis 22. With respect to any column 26 that effectively has a portion removed by the intersection of the locking and compression holes 6, 92, it should be appreciated that the column centerline 43 extends along the theoretical center of the column 26 (i.e., the center of the theoretical complete column 26). The column centerlines 43 are preferably evenly spaced along the circumference of the locking surface 24a, as shown. In the present embodiment, the column centerlines 43 of the first, second, and third columns 26a-c are located at about 120-degree intervals about axis 22. In other embodiments, the columns 26 can be un-evenly spaced along the circumference of the locking surface 24a.

Each column 26 can define a first surface 42 substantially facing the central locking hole axis 22. The first surface 42 can also be referred to as an "innermost surface" of the column 26. Thus, the first surface 42 defines crests of the threads 9. The first surface 42 of each column 26 extends between a first side 44 and a circumferentially opposed second side 45 of the column 26, with the column centerline 43 equidistantly spaced therebetween. The portions of the internal threads 9 that traverse the columns 26a-c are configured to provide the primary locking threaded engagement (intermeshing) with the exterior threads on the head of the locking screw. The first and second sides 44, 45 of each column 26 can define interfaces between the column 26 and the circumferentially adjacent recesses 28. The plate threads 9 extend through the columns 26 and at least portions of the recesses 28. For example, the threads 9 can circumferentially traverse each of the columns 26 and recesses 28 in an uninterrupted fashion along the circumference of the locking surface 24a. The internal threads 9, columns 26, and recesses 28 can be configured as more fully described in the '708 Reference.

The locking hole 6 defines a hole shape (also referred to as a "horizontal hole profile" or "hole profile") in a horizontal reference plane X-Y. It should be appreciated that the horizontal hole profiles referred to herein specifically refer to a theoretical shape of a "base version" of the locking hole 6, meaning a theoretical version of the locking hole 6 that is not intersected by a compression hole 92. In the present embodiment, at least an axial portion of the locking hole 6 has a generally polygonal horizontal hole profile. In particular, the locking hole 6 of the present embodiment has a trigon (i.e., generally triangular) horizontal profile, although in other embodiments the locking hole 6 can have other types of polygonal horizontal profiles (e.g., rectangle, pentagon, hexagon, etc.), or can have a circular horizontal profile, as discussed in more detail below. The first column 26a of the present embodiment is aligned with the longitudinal axis 97. The threads 9 also preferably extend along respective thread path(s) that corresponds to the horizontal profile of the locking hole 6. In the illustrated embodiment, the first surfaces 42 of the columns 26 have linear horizontal profiles corresponding to "sides" of the trigon, while the recesses 28 effectively define the "corners" of the trigon, each as viewed in the horizontal reference plane X-Y. Accordingly, the columns 26 and recesses 28 of the present embodiment can also be referred to respectively as "sides" and "corners" 28 of the trigon-shaped locking hole 6.

The locking hole 6 defines a locking hole radius R1 measured orthogonally from the central locking hole axis 22 to the first surfaces 42 of the respective columns 26 (or to the theoretical first surface 42 of any column 26 interrupted by the intersection boundary 119, such as the second and third columns 26b, 26c in the illustrated embodiment). The locking hole 6 also defines a lateral dimension Y1 measured along a lateral locking hole axis 23 that is oriented along the lateral direction Y and intersects the central locking hole axis 22.

Figure 1D:
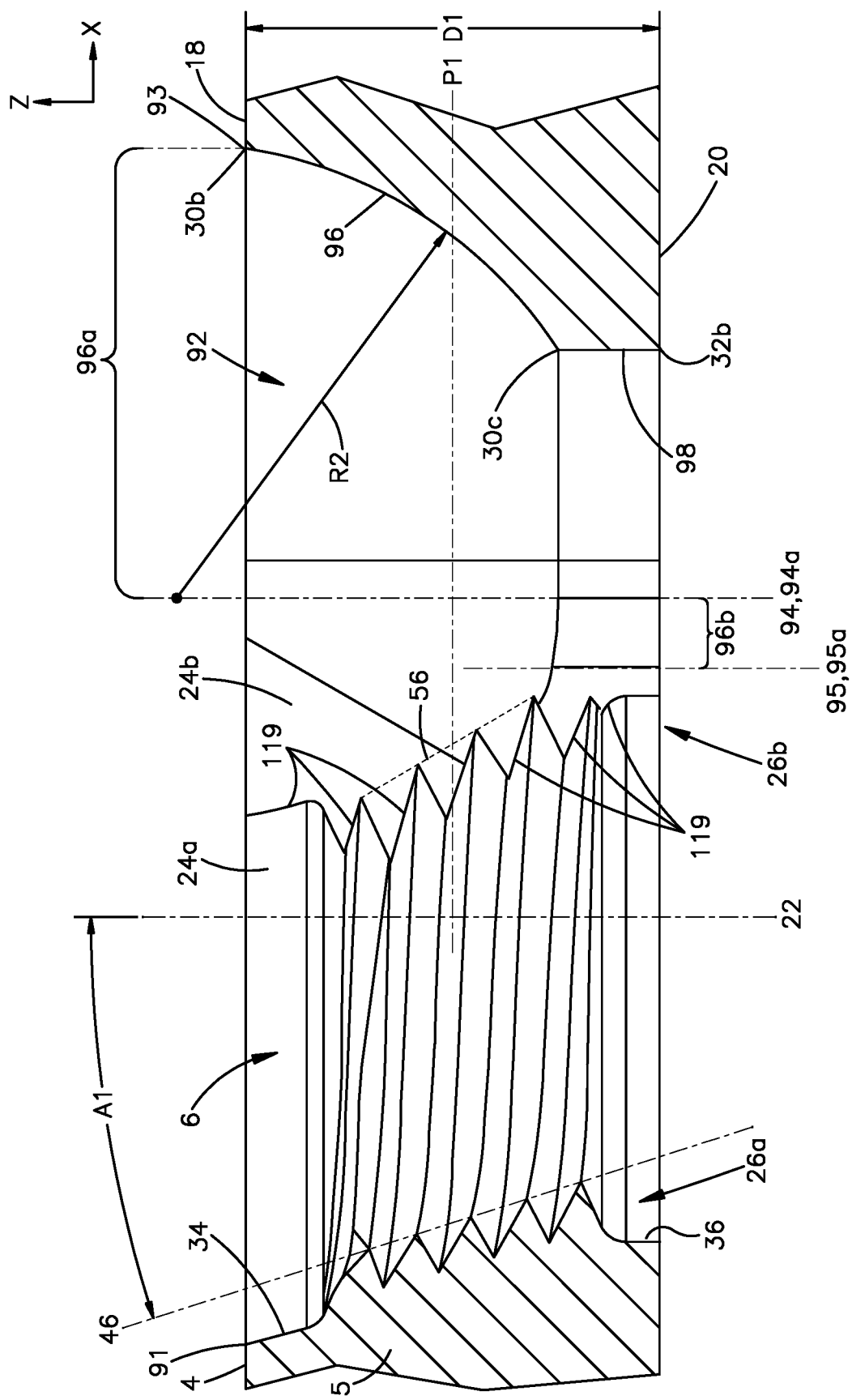
FIG. 1D is a sectional side view of the bone plate taken along section line 1D-1D in FIG. 1B.

Referring now to FIG. 1D, in a cross-sectional reference plane that extends along axes 22 and 97 (and thus along the longitudinal and transverse directions X, Z), crests of the threads 9 extend along a crest trajectory axis 46. In the present embodiment, the crest trajectory axis 46 is linear, and can be oriented at an acute crest trajectory angle A1 relative to the central hole axis 22. The crest trajectory angle A1 can be in a range of about 5 degrees to about 30 degrees, and more particularly in a range of about 10 degrees to about 20 degrees, and preferably in a range of about 13 degrees to about 17 degrees.

The combi-hole 90 defines a reference midplane P1 that is orthogonal to the central locking hole axis 22 and intersects axis 22 at a location thereof that is equidistantly spaced between the upper and bone-facing surfaces 18, 20 with respect to the transverse direction Z. Because the respective geometries of the locking hole 6 and the compression hole 92 change along the hole depth, the reference midplane P1 is a particularly useful reference feature for discussing dimensional features of the locking and compression holes 6, 92. For example, although the locking hole radius R1 and the lateral dimension Y1 can be measured at any hole depth, the following discussion of these dimensions refers to their respective measurements in the reference midplane P1.

With continued reference to FIG. 1D, the compression hole 92 include a primary surface portion 96 of the compression surface 24b. The primary surface portion 96 is also referred to herein as a "countersink" 96. The countersink 96 extends axially downward into the compression hole 92 from the upper perimeter 30b toward one or more secondary surface portions 98 of the compression surface 24b, which in turn extend axially downward to the lower perimeter 32b. An intermediate perimeter 30c of the compression surface 24b can define an interface between the countersink 96 and the one or more secondary surface portions 98. Accordingly, the intermediate perimeter 30c of the compression surface 24b can also define a lower perimeter of the countersink 96, and can thus also be referred to herein as the "lower countersink perimeter" 30c. As shown in FIGS. 1B-1C, the countersink 96 extends along the circumferential direction C2 from the intersection boundary 119 on the first side 31 of the combi-hole 90 to the intersection boundary 119 on the second side 33 of the combi-hole 90. Preferably, at least an entirety of the countersink 96 outside the hole intersection zone 120 is smooth and unthreaded.

As shown in FIG. 1D, the countersink 96 preferably has a concave surface profile in a refence plane that extends along the central compression hole axis 94. For example, in a longitudinal reference plane 99 (FIG. 1B) that extends along the intersection axis 97 and axis 94 (and thus along the longitudinal and transverse directions X, Z), the surface profile of the countersink can be defined by a segment of a circle having radius R2, which can also be referred to herein as the "countersink profile radius" R2. The countersink profile radius R2 can be substantially constant along at least a circumferential portion of the countersink 96. For example, in the illustrated embodiment, the countersink profile radius R2 can be substantially constant along a circumferential portion 96a of the countersink 96 that extends between the second end 93 and a first lateral reference plane 94a extending along axis 94 (and thus along the transverse direction Z) and also along the lateral direction Y. The surface profile of the countersink 96 along circumferential portion 96a preferably corresponds to the exterior surface of the head of the compression screw, as described in more detail below. Additionally, the surface profile of the countersink 96 can vary along one or more circumferential portions thereof, as described in more detail below.

As shown in FIGS. 1B and 1C, the compression hole 92 defines a hole shape (or "horizontal hole profile" or "hole profile") in a horizontal reference plane X-Y. Similar to the locking hole 6 described above, the "horizontal hole profile" of the compression hole 92 refers specifically to a theoretical shape of a "base version" of the compression hole 92, meaning a theoretical version of the compression hole 92 that is not intersected by a locking hole 6. For example, the compression hole 92 can have a hole profile that is generally circular, round, oval, elliptical, obround (i.e., a rectangle with semicircles at opposite ends, also referred to as a "stadium" or "discorectangle"), or a shape having various features of the foregoing.

With specific reference to the illustrated embodiment, the compression hole 92 has an obround-like hole profile. It should be appreciated that this embodiment is provided as a non-limiting example of intersecting locking hole 6 and compression hole 92 geometries to provide dynamic compression in a direction from the compression hole 92 toward the locking hole 6. In this embodiment, the compression hole 92 defines a second axis 95 that is parallel with the central compression hole axis 94. The second axis 95 intersects the intersection axis 97 as a location thereof between axis 22 and 94 (and thus within the intermediate zone 115). The second axis 95 is spaced from axis 94 at a distance LA2 along the intersection axis 97. A second lateral reference plane 95a extends along axis 95 (and thus along the transverse direction Z) and along the lateral direction Y. Along circumferential portion 96a, the countersink 96 has a semi-circular hole profile, which preferably is complimentary with the exterior surface of the head of the compression screw. In this manner, the head can engage circumferential portion 96a of the countersink 96 in complimentary fashion when fully seated within the compression hole 92. In this longitudinal region (along circumferential portion 96a), the upper and lower perimeters 30b, 30c extend circumferentially along parallel curves. In a longitudinal region 96b between reference planes 94a and 95a, the upper perimeter 30b can transition to a horizontal profile that deviates from that of the lower countersink perimeters 30c. In particular, in region 96b, the lower countersink perimeter 30c extends parallel with itself along the first and second sides 31, 33 of the combi-hole 90. In the hole intersection zone 120, the lower countersink perimeter 30c extends again along a semi-circular hole profile. Within the longitudinal region between reference planes 94a and 95a, the upper perimeter 30b extends from reference plane 94a to opposite transition locations 94b on the first and second sides 31, 33 of the combi-hole 90. At these transition locations 94b, the upper perimeter 30b transitions to linear paths that converge toward each other at an acute angle as they extend to the intersection boundary 119. In this manner, from the transition locations 94b to the intersection boundary 119, the upper perimeter 30b effectively defines the non-parallel sides of an isosceles trapezoid. For example, moving from the second end 93 toward the first end 91 of the combi-hole 90, the upper perimeter 30b approaches the transition locations 94b along a circular path and exits the transition locations 94b along respective tangent lines (i.e., tangent to the circular path at which the upper perimeter 30b intersects transition locations 94b).

The foregoing intersecting geometries of the countersink 96 and the locking surface 24a are favorable for causing dynamic compression when a compression screw is inserted eccentrically within the intermediate zone 115 (that is, inserted along an insertion axis 52 located between axis 22 and axis 94). As shown, in the hole intersection zone 120, the countersink 96 intersects and thus truncates portions of the threads 9 on the first and second sides 31, 33. It should be appreciated that the intersection boundary 119 can extend beyond the intermediate zone 115 toward the first end 91 of the combi-hole 90. In other embodiments, the intersection boundary 119 can be entirely located within the intermediate zone 115.

The intersecting geometries of the countersink 96 and the locking surface 24a along the intersection boundary 119 defines guide formations 55 opposite each other on the first and second sides 31, 33 of the combi-hole 90. The guide formations 55 can also be referred to herein as "chamfers", "ramps" or "rails". The guide formations 55 are configured to provide dynamic compression (i.e., to translate the plate 4) in a first translation direction T1 responsive to engagement (i.e., contact) with the head of a compression screw inserted along an eccentric screw insertion axis 52 located between axis 22 and 94 (i.e., within the intermediate zone 115). In particular, the guide formations 55 define contact interfaces or paths between the interior surface 24 of the combi-hole 90 and the head of the compression screw. The guide formations 55 extend along respective guide axes 56 that extend along the intersection boundary 119 on the first and second sides 31, 33 of the combi-hole 90. In the illustrated embodiment, the guide axes 56 are shown intersecting the respective roots along the intersection boundary 119. As shown in FIG. 1C, the guide axes 56 can be linear as viewed orthogonally from a horizontal reference plane X-Y. In such embodiments, the guide axes 56 on the opposite sides 31, 33 of the combi-hole 90 can each define a horizontal guide angle A2, as measured between the respective guide axis 56 and the intersection axis 97 in the horizontal reference plane X-Y. The horizontal guide angle A2 can be in a range from about 10 degrees to about 80 degrees, and more particularly in a range from about 25 degrees to about 65 degrees, and more particularly in a range from about 40 degrees to about 50 degrees. In other embodiments, at least a portion of, and up to an entirety of, each horizontal guide axis 56 can extend along a curved path as viewed orthogonally from a horizontal reference plane X-Y. In such embodiments, the horizontal guide angle A2 can be measured from the intersection axis 97 to a reference tangent line that intersects the guide axis 56 at the reference midplane P1.

The guide formations 55 each have at least a directional component in the offset direction (i.e., the second longitudinal direction X2), thus guiding the first translation direction T1 such that it has at least a directional component in the first longitudinal direction X1, at least when the insertion axis 52 is offset from axis 22 at least at a minimum offset distance O in the second longitudinal direction X2. Accordingly, the second longitudinal direction X2 of the present embodiment can also be referred to as the "offset direction". The minimum offset distance O refers to the shortest offset distance that will result in dynamic compression in the first longitudinal direction X. The minimum offset distance O can be defined as the shortest distance between the central locking hole axis 22 and the guide formations 55 along the longitudinal direction X. Stated differently, the minimum offset distance O can be the shortest longitudinal distance from the central locking hole axis 22 to the hole intersection zone 120 (i.e., to the intersection boundary 119). The minimum offset distance O can be reduced or increased by narrowing or widening, respectively, the horizontal guide angle A2. In this manner, the guide formations 55 are preferably configured to direct or "funnel" or otherwise influence the translation direction T1 in the first longitudinal direction X1 as the head advances axially downward within the combi-hole 90, including when the insertion axis 52 is also laterally offset from (i.e., spaced from the intersection axis 97 along the lateral direction Y). It should be appreciated that higher axial loads on the screw head and/or higher torques on the screw head during screw insertion into underlying bone can require steeper (i.e., wider) horizontal guide angles A2 to enhance sliding (i.e., dynamic compression) performance of the plate 4. Additionally, the combi-hole 90, particularly the countersink 96 and intersection boundary 119 thereof, are preferably configured such that the plate 4 translation results in the central compression hole axis 94 being substantially colinear with the central axis 52 of the compression screw when the head is fully seated in the compression hole 92.

A ratio of the axis separation distance LA1 to the hole length L can be in a range from about 0.24:1 to about 0.50:1, and more particularly in a range from about 0.30:1 to about 0.38:1, and preferably in a range from about 0.33 to about 0.35. A ratio of the radius R1 to the axis separation distance LA1 is in a range from about 0.75:1 to about 1.25:1, and more particularly in a range from about 0.85:1 to about 1.15:1, and more particularly in a range from about 0.98:1 to about 1.02:1. A ratio of the minimum offset distance O to radius R1 (as measured in the reference midplane P1) is in a range from about 0.0:1 to about 0.95:1, and more particularly in a range from about 0.125:1 to about 0.225:1, and more particularly in a range from about 0.16:1 to about 0.20:1.

Figure 2:
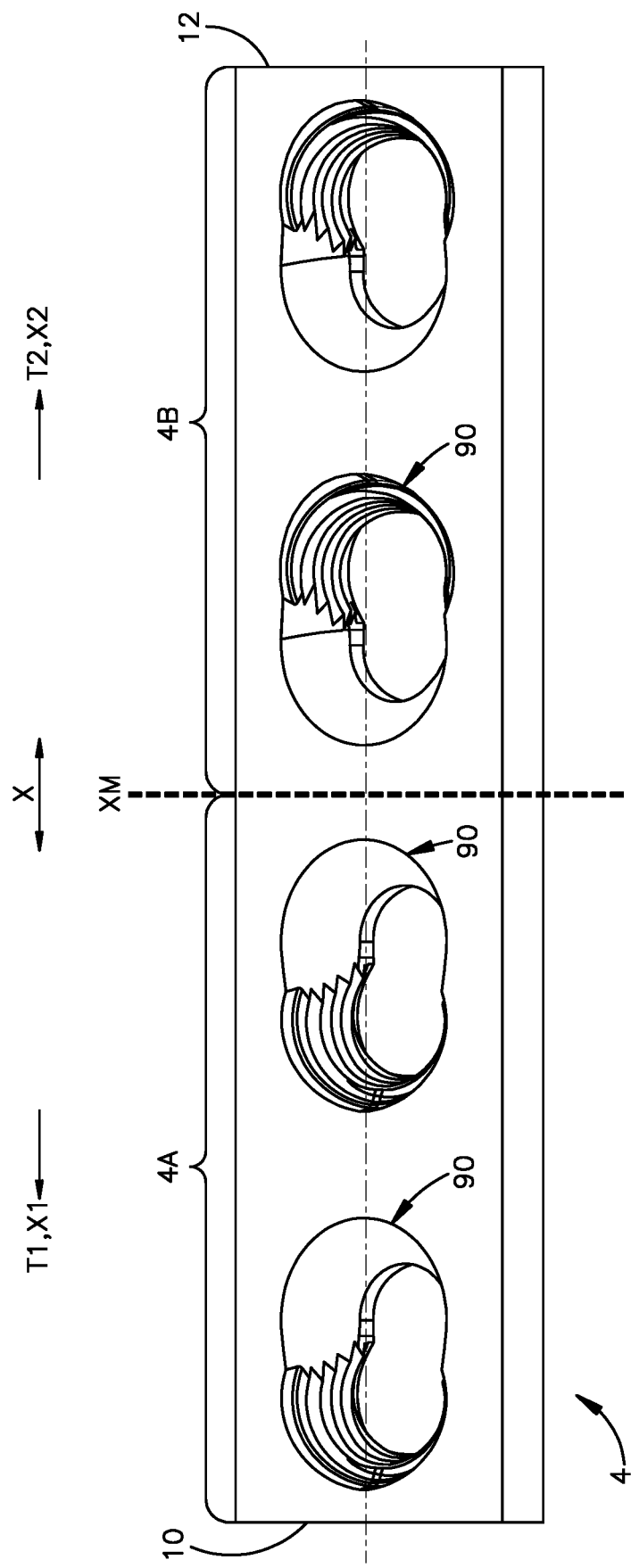
FIG. 2 is a top view of a bone plate having multiple combi-holes configured according to the combi-hole illustrated in FIGS. 1A-1D.

Referring now to FIG. 2, an example embodiment of a bone plate 4 is shown having a plurality of combi-holes 90 according to the present disclosure. The plate 4 has a first end 10 and a second end 12 spaced from each other along the longitudinal direction X. The plate 4 defines a longitudinal axis 3 oriented along the longitudinal direction X. The combi-holes 90 can be arranged in the plate 4 in a manner providing the plate 4 with multi-directional dynamic compression. For example, the combi-holes 90 can be arranged in a first group of combi-holes 90 along a first longitudinal region 4a of the plate 4 and a second group of combi-holes 90 along a second longitudinal region 4b of the plate 4. In this example, the first and second longitudinal regions 4a, 4b extend to a common boundary at a longitudinal midpoint XM of the plate 4. Each combi-hole 90 of the first group is oriented to provide dynamic compression (i.e., to translate the plate 4) in a first translation direction T1, such as in the longitudinal direction X1 extending from the first end 10 to the second end 12 of the plate 4. Each combi-hole 90 of the second group is oriented to provide dynamic compression in a second translation direction T2, such as in the longitudinal direction X2 extending from the second end 12 to the first end of the plate 4. It should be appreciated that the arrangement and orientation of the combi-holes 90 can be adapted as needed to provide the plate 4 with dynamic compression capabilities in various directions according to the needs of a particular surgical treatment.

Figure 3A:
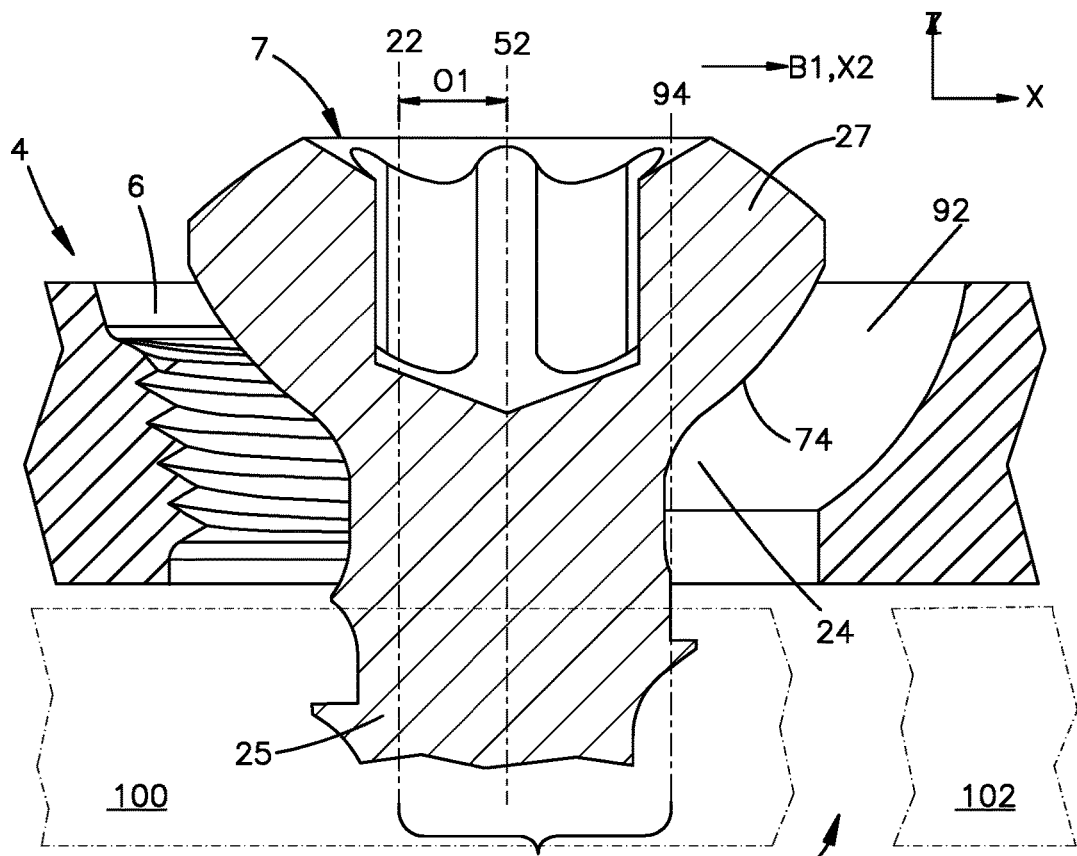
FIG. 3A is the sectional side view of the combi-hole of FIG. 1D showing a compression screw inserted eccentrically therein at a first contact position, according to an embodiment of the present disclosure.
Figure 3B:
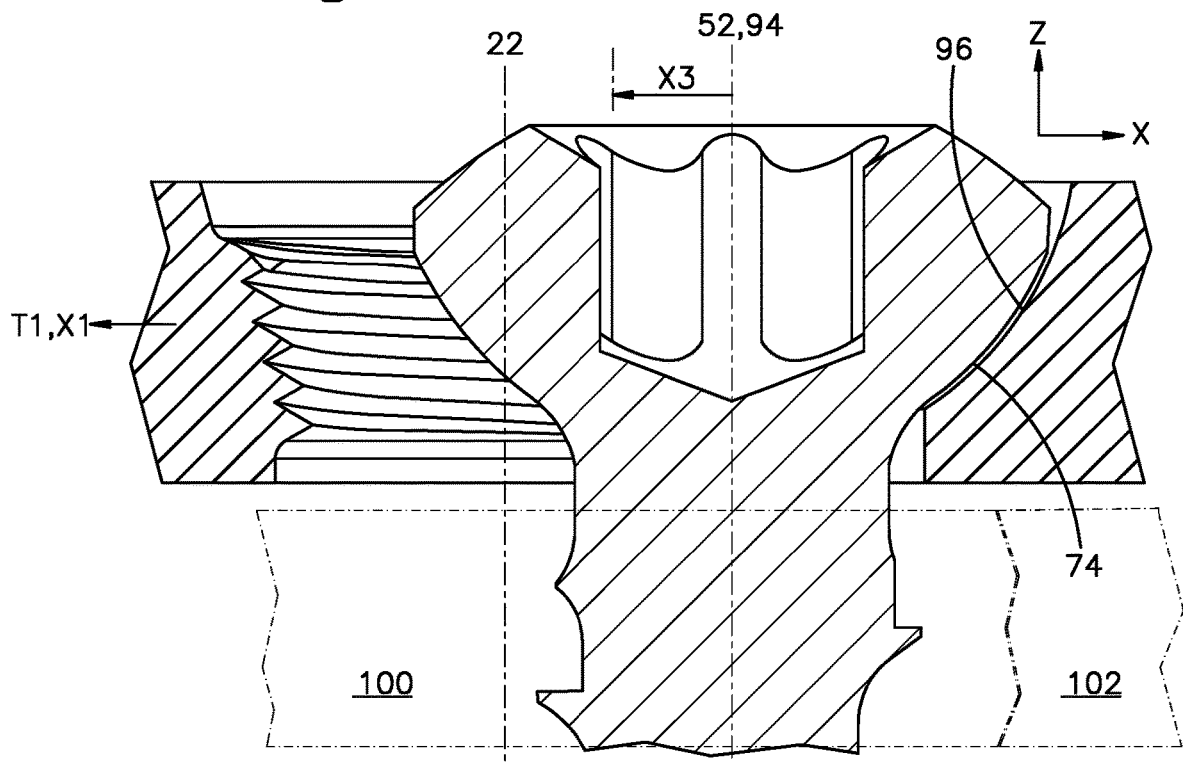
FIG. 3B is the sectional side view of the combi-hole of FIG. 1D showing the compression screw inserted eccentrically therein at a fully seated position.

Referring now to FIGS. 3A and 3B, methods of using a combi-hole 90 of the present embodiment in a bone plating operation for selective dynamic compression will now be described, according to an example technique of eccentrically inserting a compression screw 7 in the intermediate zone 115 of the combi-hole 90. During the bone plating operation, a physician can insert a shaft 25 of a compression screw 7 through the combi-hole 90 along an insertion axis 52 and drive the shaft 25 into underlying bone, such as a bone segment 100. In this example, the physician can cause the insertion axis 52 to be offset from the central locking hole axis 22 by a first offset distance O1 in an offset direction B1 (which is the second longitudinal direction X2 in this example). As shown in FIG. 3A, the physician can further drive the shaft 25 along the insertion axis 52 in a manner causing an outer surface 74 of the head 27 of the compression screw 7 to contact the interior surface 24 of the combi-hole 90 at a first position of the screw head 27 with respect to the interior surface 24. At the first position (FIG. 3A), the outer surface 74 of the screw head 27 contacts the interior surface 24 at a first initial contact location 75, such as at a pair of contact locations 75 along the intersection boundary 119 (see FIG. 1C).

As shown in FIG. 3B, after the outer surface 74 of the head 27 contacts the interior surface 24 at the first initial contact location 75 (FIG. 3A), the physician can further drive the compression screw 7 axially downward along the insertion axis 52, causing the outer surface 74 of the head 27 to travel or ride along the guide formations 55 to a second position of the screw head 27 relative to the interior surface 24, which can be a fully seated position of the screw head 27 against the countersink 96. In the fully seated position, the central axis 52 of the compression screw 7 is preferably colinear with the central compression hole axis 94. It should be appreciated that the translation distance X3 is substantially determined by the offset distance O1. For maximizing the translation distance X3, the physician can select an offset distance O1 that is substantially equivalent to the minimum offset distance O. The translation distance X3 decreases as the offset distance O1 increases. In this manner, the physician can select the suitable offset distance O1 to achieve the desired translation distance X3 for the bone plate 4 relative to the underlying bone segment 100. The interfacing geometries of the head 27 and the interior surface 24 of the combi-hole 90, such as along the guide formations 55, can provide a maximum translation distance X3 that is greater than the minimum offset distance O at a ratio in a range from about 1:1 to about 5:1, and more particularly in a range from about 2.25:1 to about 4.0:1, and more particularly in a range from about 3.0:1 to about 3.4:1. In this manner, the physician can manipulate bone plate 4 in the translation direction T1 in a manner reducing a gap G1 (FIG. 3A) between the bone segment 100 and an adjacent bone segment 102.

The combi-holes 90 of the present disclosure are versatile in that the first side 91 of the combi-hole 90 can be used to achieve dynamic compression in a second translation direction having at least a directional component in the second longitudinal direction X2. Such dynamic compression can be achieved by inserting the compression screw 7 along an insertion axis 52 at an offset distance between axis 22 and the first end 91 of the combi-hole, similar to the manner described more fully in U.S. Patent Application Ser. No. 63/107,699, filed Oct. 30, 2020, in the name of Aebi et al. ("the '699 Reference"), the entire disclosure of which is hereby incorporated by reference herein.

It should be appreciated that the configuration of the combi-holes 90 described herein provides numerous additional options for dynamic compression, including along other translation directions. For example, dynamic compression can be achieved to translate the plate 4 in the second longitudinal direction X2 by inserting the compression screw 7 along an insertion axis 52 offset from the central compression hole axis 94 in the second longitudinal direction X2.

The plate body 5, compression screws 7, and locking screws described herein can each comprise one or more biocompatible materials. By way of non-limiting examples, the plate body 5 can be formed of a material selected from a group comprising: metal, such as titanium, titanium alloys (e.g., titanium-aluminum-niobium (TAN) alloys, such as Ti-6Al-7Nb, and titanium-aluminum-vanadium (TAV) alloys such as Ti-6Al-4V, titanium molybdenum alloys (Ti—Mo) or any other molybdenum metal alloy, and nickel-titanium alloys, such as nitinol), stainless steel, and cobalt base alloys (e.g., cobalt-chrome alloys); composite materials; polymeric materials; ceramic materials; and/or resorbable materials, including resorbable versions of the foregoing material categories (metals, composites, polymers, ceramics). Also by way of non-limiting examples, the compression screws 7 and locking screws can be formed of a material selected from a group comprising: metal, such as titanium, titanium alloys (e.g., TAN alloys, TAV alloys, such as Ti-6Al-4V, titanium molybdenum alloys (Ti—Mo) or any other molybdenum metal alloy, and nickel-titanium alloys, such as nitinol), stainless steel, cobalt base alloys (e.g., cobalt-chrome alloys); composite materials; polymeric materials; ceramic materials; and/or resorbable materials, including resorbable versions of the foregoing material categories (metals, composites, polymers, ceramics). Preferably, the material of the compression screws 7 and locking screw ha a hardness that is greater than that of the material of the plate body 5. This parameter contributes to the threaded locking characteristics and the dynamic compression characteristics described throughout the present disclosure. Preferably, the plate body 5 primarily or entirely comprises titanium and the compression screws 7 and locking screws primarily or entirely comprise TAN. It should be appreciated, however, that other material compositions of the bone plates 4 and/or the screws are within the scope of the present disclosure.

Moreover, surfaces of the plate body 5 and/or the screws can optionally be subjected to one or more processes, such as coating, treating, and/or finishing processes, which can be performed to provide such surfaces, or the underlying subject body material, with certain characteristics, such as to adjust hardness, softness, and/or friction parameters of the body material, as more fully described in the '105 and '708 References.

It should be appreciated that the various parameters of the combi-holes 90 described above are provided as exemplary features for adapting the combi-holes 90 to achieve selective dynamic compression or locking engagement with the heads of respective compression screws and locking screws. These parameters can be adjusted as needed without departing from the scope of the present disclosure.

It should also be appreciated that in additional embodiments, the interior surface 24 of any combi-hole 90 can be defined by an insert plate body (e.g., an "insert" or "inlay") that is fitted within an axial aperture or receptacle of the plate body 5. In such embodiments, the bone plate 4 can be provided in a kit that includes a plurality of interchangeable inserts having different combi-hole shapes and geometries, such that the physician can select the particular insert having the desired dynamic compression characteristics needed.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. In particular, one or more of the features from the foregoing embodiments can be employed in other embodiments herein. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone plate, comprising:
a plate body defining an interior surface that defines a combination hole comprising a locking hole and a compression hole that intersect one another and each extends from an outer surface of the plate body to a bone-facing surface of the plate body, the locking hole defining a central locking hole axis and the compression hole defining a central compression hole axis, wherein the central compression hole axis is spaced from the central locking hole axis in an offset direction, and the offset direction is oriented along an intersection axis that intersects the central locking hole axis and the central compression hole axis,
the plate body further defining a locking surface that defines the locking hole and at least one locking structure within the locking hole, and the plate body further defining a compression surface that defines the compression hole,
wherein an intersection boundary between the locking surface and the compression surface defines guide formations opposite each other on first and second sides of the combination hole, the guide formations extend along respective guide axes that each define a guide angle measured between the respective guide axis and the intersection axis,
wherein the the guide formations are configured to contact a head of a compression bone fixation member that is inserted into the combination hole along an insertion axis which in turn causes the bone plate to translate in a translation direction opposite the offset direction until the head is seated against the compression surface, wherein the insertion axis is in the locking hole and offset from the central locking hole axis in a direction having a directional component in the offset direction, and
wherein each of the respective guide axes is sloped toward the compression hole as it extends in a direction that is defined from the outer surface of the plate body to the bone-facing surface of the plate body.

2. The bone plate of claim 1, wherein the intersection axis is oriented along a longitudinal direction, the combination hole having a first end and a second end opposite each other along the longitudinal direction, and the offset direction is substantially parallel with the longitudinal direction.

3. The bone plate of claim 2, wherein the first side and the second side of the hole are spaced from each other along a lateral direction substantially perpendicular to the longitudinal direction, wherein the first and second sides are located opposite each other with respect to a reference plane that extends along the intersection axis and along a transverse direction that is substantially perpendicular to the longitudinal and lateral directions, wherein the combination hole is configured such that the head slides along a pair of contact paths along the respective guide axes during the translation.

4. The bone plate of claim 3, wherein the hole further defines an intermediate zone between the central locking hole axis and the central compression hole axis with respect to the longitudinal direction, the interior surface defines a neck at the intersection boundary, and a minimum lateral dimension of the combination hole between the first and second sides thereof within the intermediate zone occurs at the neck.

5. The bone plate of claim 4, wherein the intersection boundary extends beyond the intermediate zone toward the first end of the combination hole.

6. The bone plate of claim 4, wherein the intersection boundary is entirely contained within the intermediate zone.

7. The bone plate of claim 4, wherein the locking surface further defines:
first, second, and third columns sequentially located about the central locking hole axis;
a first corner extending from a second side of the first column to a first side of the second column;
an additional corner extending from a second side of the third column to a first side of the first column;
a gap between the second and third columns along the lateral direction, the gap located at the neck, wherein the locking hole and the compression hole are open to each other through the gap,
wherein the at least one locking structure comprises threads that traverse each of the columns and at least portions of the first corner and the additional corner.

8. The bone plate of claim 7, wherein the first, second, and third columns are arranged in a polygonal pattern, the intersection axis intersects the first column, wherein the second and third columns are substantially equidistantly spaced from the reference plane along the lateral direction, and at least some of the threads along each of the first and second sides extend to the intersection boundary such that interface edges between the locking surface and the compression surface along each of the first and second sides include edges of fully formed thread profiles of the threads.

9. The bone plate of claim 1, wherein the combination hole defines an axis separation distance between the central locking hole axis and the central compression hole axis along a longitudinal direction oriented along the intersection axis, and the combination hole further defines a hole length between first and second ends of the combination hole along the longitudinal direction, such that, in a reference midplane that is orthogonal to the central locking hole axis and intersects the central locking hole axis at a location that is equidistantly spaced between the outer surface and the bone-facing surface with respect to a transverse direction that is substantially parallel with the central locking hole axis, a ratio of the axis separation distance to the hole length is in a range of about 0.24:1 to about 0.38:1.

10. The bone plate of claim 9, wherein, in the reference midplane, the locking hole defines a locking hole radius measured from the central locking hole axis to the nearest portion of the locking surface, and a ratio of the locking hole radius to the axis separation distance is in a range of about 0.75:1 to about 1.25:1.

11. The bone plate of claim 10, wherein the compression surface defines an arcuate profile in a reference plane that extends along the central compression hole axis.

12. The bone plate of claim 9, wherein, in the reference midplane, the combination hole defines:
 a locking hole radius measured from the central locking hole axis to the nearest portion of the locking surface; and
 a minimum offset distance in the offset direction that will cause the translation, wherein a ratio of the minimum offset distance to the locking hole radius is in a range from about 0.125:1 to about 0.225:1.

13. The bone plate of claim 1, wherein the combination hole is configured such that the translation causes the insertion axis to be substantially colinear with the central compression hole axis when the head is fully seated in the compression hole.

14. The bone plate of claim 1, wherein the guide axes converge toward one another such that a location of minimum distance between the guide axes is spaced from the central compression hole axis in the offset direction.

15. The bone plate of claim 1, wherein, in a plane that is orthogonal to the central compression hole axis, the compression surface comprises 1) a curved surface, and 2) first and second linear surfaces that extend from the curved surface to the locking structure at the first and second sides, respectively, of the combination hole, and the first and second linear surfaces are defined entirely between the central locking hole axis and the central compression hole axis with respect to a longitudinal direction that is parallel with the intersection axis.

16. The bone plate of claim 1, wherein the intersection boundary comprises first and second intersection boundaries that are opposite each other with respect to the intersection axis, and are aligned with each other along a direction perpendicular to the intersection axis.

* * * * *